(12) United States Patent
Filsouf

(10) Patent No.: US 7,757,327 B2
(45) Date of Patent: Jul. 20, 2010

(54) ELECTRIC TOOTHBRUSH

(76) Inventor: Ehsan Filsouf, 51-1 Northern Heights Drive, Richmond Hill, Ontario (CA) L4b 4C9

( * ) Notice: Subject to any disclaimer, the term of this patent is extended or adjusted under 35 U.S.C. 154(b) by 28 days.

(21) Appl. No.: 12/334,695

(22) Filed: Dec. 15, 2008

(65) Prior Publication Data
US 2009/0313773 A1 Dec. 24, 2009

Related U.S. Application Data

(63) Continuation-in-part of application No. 11/322,214, filed on Jan. 3, 2006, now Pat. No. 7,464,430.

(51) Int. Cl.
*A61C 17/22* (2006.01)
(52) U.S. Cl. .............. 15/22.1; 15/22.4; 15/23
(58) Field of Classification Search .......... 15/22.1, 15/22.4, 23
See application file for complete search history.

(56) References Cited

U.S. PATENT DOCUMENTS

| 2,662,239 | A | | 12/1953 | Grover |
|---|---|---|---|---|
| 4,149,291 | A | | 4/1979 | Stoltz |
| 4,275,479 | A | | 6/1981 | Korhonen |
| 4,882,801 | A | | 11/1989 | Benz |
| 4,979,387 | A | | 12/1990 | Dittmar |
| 5,732,433 | A | * | 3/1998 | Gocking et al. ............. 15/28 |
| 5,974,296 | A | | 10/1999 | Suketomo et al. |
| 6,047,711 | A | | 4/2000 | Wagner |
| 2005/0091773 | A1 | | 5/2005 | Gavney, Jr. et al. |

* cited by examiner

*Primary Examiner*—Shay L Karls
(74) *Attorney, Agent, or Firm*—Cantor Colburn LLP

(57) ABSTRACT

An electric toothbrush in which the brushing head moves in an elliptical motion such that, on the brushing stroke, the bristles are proximate the teeth, and in the recovery portion of the cycle the bristles are pulled away from the teeth. A position sensitive switch automatically switches from a forward to a reverse operation of the electric motor, depending on the positioning of the toothbrush in a user's hand, allowing the user to brush both the upper and lower teeth using a stroke carrying the bristles from the gum line to the ends of the teeth, as is recommended by dental professionals, without having to move the toothbrush from hand to hand or manually move the switch from the forward to the reverse positions. A bridge pad engages the face of the teeth, maintaining a proper distance between the teeth and bristles during the elliptical rotation of the brush head.

4 Claims, 17 Drawing Sheets

ELECTRIC TOOTHBRUSH

The present invention is a continuation-in-part of U.S. application Ser. No. 11/322,214 filed on Jan. 3, 2006, currently allowed.

BACKGROUND OF THE INVENTION

1. Field of the Invention

The present invention relates to electric toothbrushes. More particularly, the invention comprises an electric toothbrush having a reversible, elliptical rotation pattern of the brushing head, allowing strokes which brush away from the gums, regardless of which hand the user uses or whether he is brushing the upper or lower teeth.

2. Description of the Prior Art

Electric toothbrushes are well known in the art. Most electric toothbrushes, however, provide only an up and down motion, thereby brushing into the gum on half of the brush strokes. Most of the brushes which do provide a rotary motion, and thus only brush away from the gum, as advised by dental professionals, present other problems.

U.S. Pat. No. 5,974,296, issued to Tit Shing Wong on Aug. 18, 1998, discloses an ELECTRIC TOOTHBRUSH, having a reversible, rotary brush head activated by a switch at the brush head, which is placed inside the mouth. By contrast, the switch of the present invention is contained within the handle of the toothbrush and is activated by the position of the toothbrush in the user's hand, and the brushing action of the brush head is performed with a stroking motion as opposed to a rotary motion. The present invention further includes a spacer to maintain the brush at a proper distance from the teeth during the brushing and recovery strokes, not found in Wong's brush.

Celso Caroli discloses an ELECTRICALLY DRIVEN CONTINUOUS TOOTH BRUSH in U.S. Pat. No. 4,275,479 issued on Jun. 30, 1981. A reversible, rotating brush head is controlled by a manual switch controlled by the user's fingers. By contrast, the switch of the present invention is contained within the handle of the toothbrush and is activated by the position of the toothbrush in the user's hand, and the brushing action of the brush head is performed with a stroking motion as opposed to a rotary motion. The present invention further includes a spacer to maintain the brush at a proper distance from the teeth during the brushing and recovery strokes, not found in Caroll's brush.

A METHOD AND APPARATUS FOR CONVERTING A POWER-DRIVEN TOOTHBRUSH INTO A POWER-DRIVEN FLOSSING DEVICE is disclosed in U.S. Pat. No. 6,047,711, issued to Daniel A. Wagner on Apr. 11, 2000. The toothbrush and flosser, as described do not provide elliptical rotation of the head or means of spacing the brushes away from the teeth.

None of the above inventions and patents, taken either singly or in combination, is seen to describe the instant invention as claimed.

SUMMARY OF THE INVENTION

The present invention provides an electric toothbrush which has a reversible, elliptical brushing motion which allows a user to brush from the gums to the tips of the teeth, regardless of which hand he is using or whether he is brushing the upper or lower teeth. The brush bristles are split such that they extend on either side of a soft spacer pad which may be rested against the teeth. The spacer maintains the bristles at a given distance away from the teeth, such that they brush against the teeth on the near, brushing stroke, portion of an elliptical orbit about an axis of the shaft while pulling away from the teeth on the far, recovery, portion of the elliptical orbit. An automatic, position sensitive switch allows the brush shaft to change the direction of its elliptical rotation about its axis, allowing a user to switch the brushing direction of the bristles by a simple change of the angle of the wrist in order to change from brushing the left or right or the front or the back of the teeth. A three position switch on the handle allows the user to selectively reverse the motor for brushing the upper teeth or the lower teeth.

Accordingly, it is a principal object of the invention to provide an electric toothbrush which is capable of brushing both the upper and lower teeth, with the bristles stroking away from the gums, as is recommended by dental professionals.

It is another object of the invention to provide an electric toothbrush which is able to change the direction of the bristle stroke by a simple change of wrist position.

It is a further object of the invention to provide an electric toothbrush having an spacer element to maintain the brush shaft away from the teeth, allowing the bristles to brush the teeth on the brushing portion of the cycle while maintaining the proper distance between the brush head and the teeth, and thereby assuring that the bristles completely detach from the teeth during the recovery portion of the brushing cycle.

Still another object of the invention is to provide an electric toothbrush which may, optionally, be either AC or DC operated.

An additional object of the invention is to provide an electric toothbrush which is relatively light weight, yet durable.

It is again an object of the invention to provide an electric toothbrush which is relatively economical to purchase and operate.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
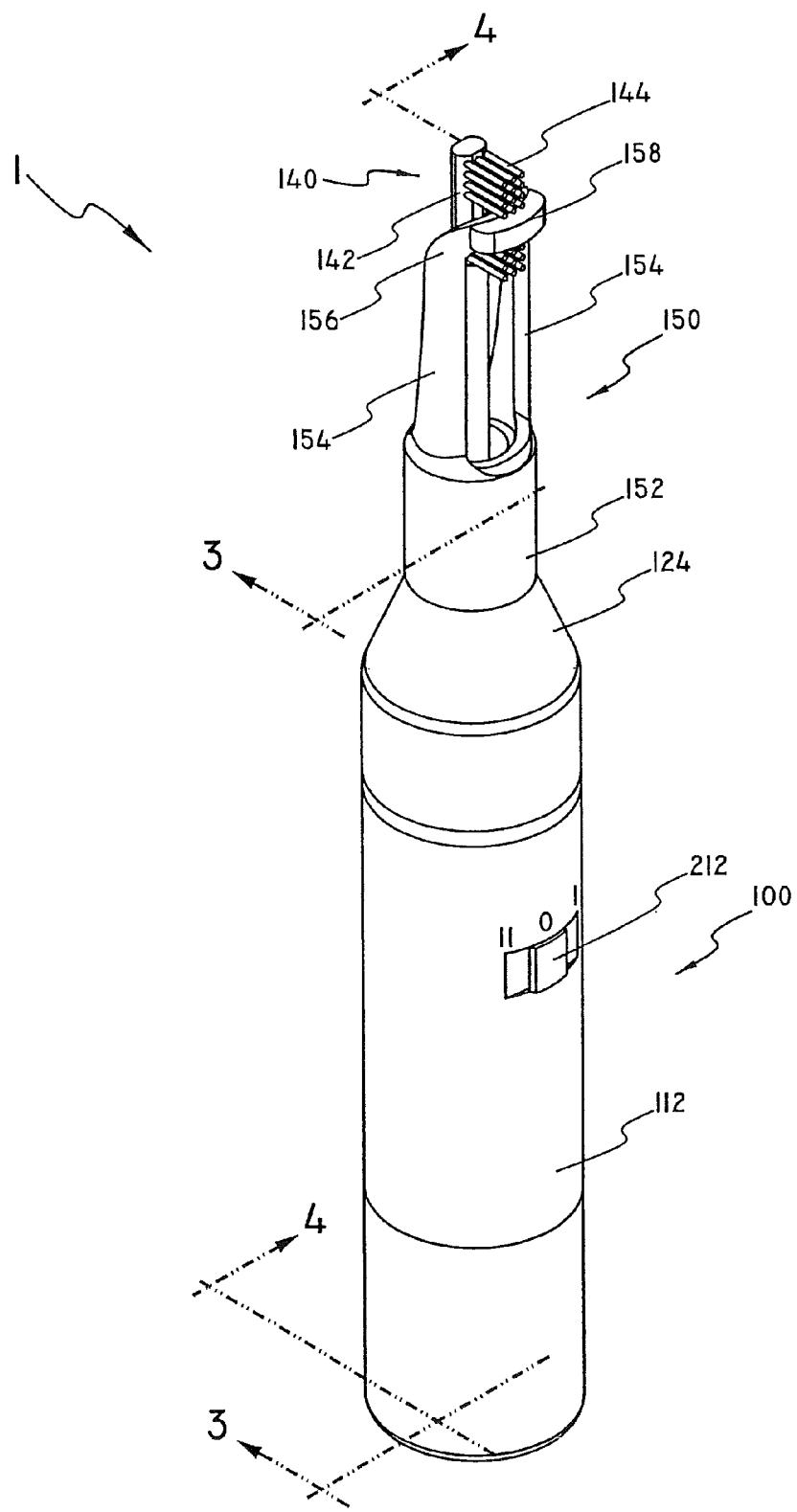
FIG. 1 is a perspective view of the toothbrush of the present invention.
Figure 2:
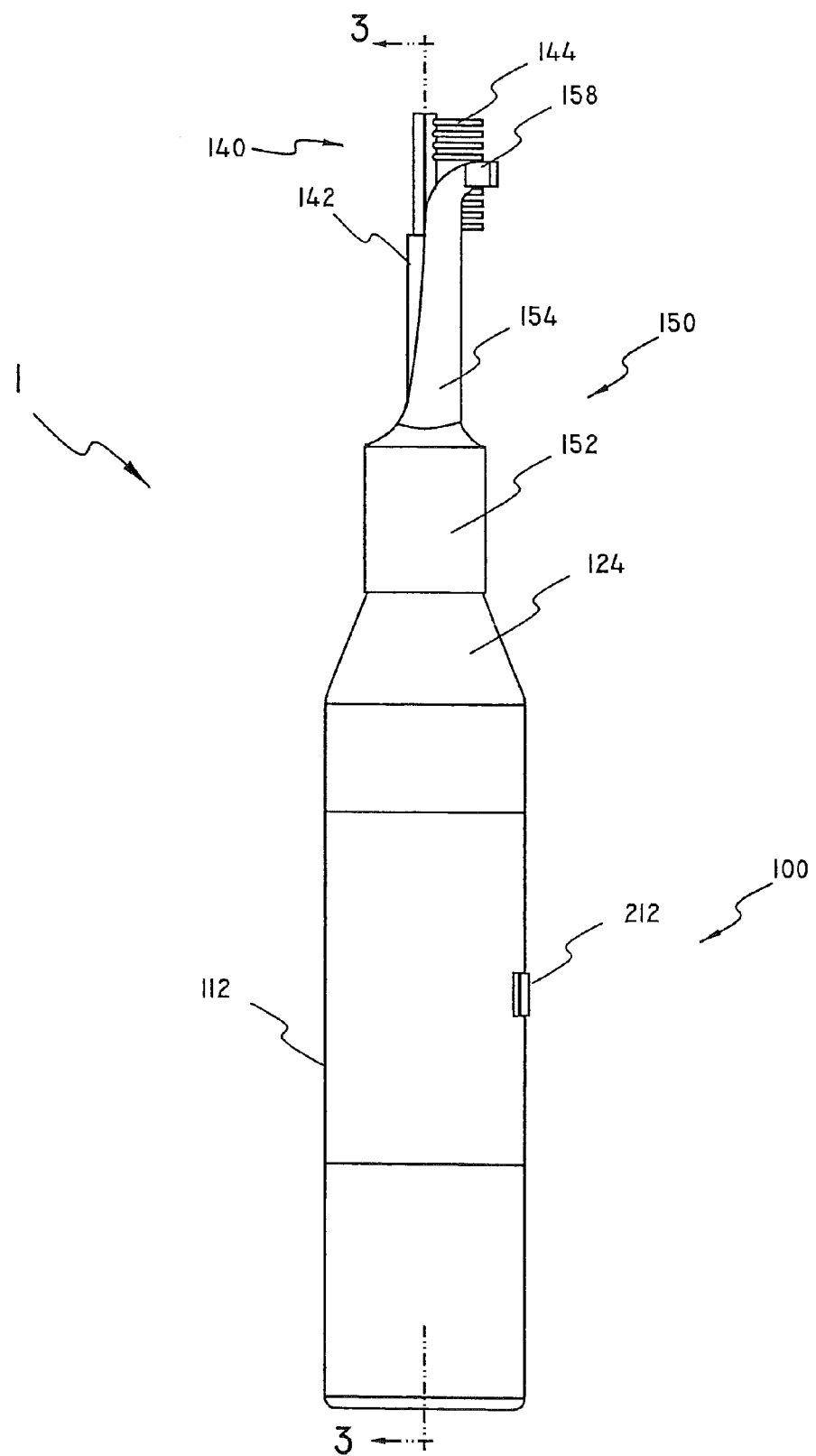
FIG. 2 is a side view of the toothbrush of the present invention.

Toothbrush 1, generally presented at FIGS. 1 and 2, includes a handle 100 and a brush head 140. Handle 100 is further composed of a body housing 112 and shoulder housing 124, while brush head 140 is further composed of brush shaft 142 and bristles 144. A switch 212 controlling motor 210 (FIG. 5) located within the body housing 112 is located on the body housing 112. The body housing 112 is substantially cylindrical in shape, having a closed lower end and an open upper end. It would be evident to one of ordinary skill in the art, however, that the body housing 112 may take anyone of a variety of other shapes without departing from the spirit of the invention. The shoulder housing 124 is substantially frustoconical in shape having a larger, open lower end adapted to mate with the open upper end of the body housing 112 and a substantially closed upper end with an aperture centered therein allowing the passage of a brush drive shaft (to be detailed herein below).

Still referring to FIGS. 1 through 4, a brush spacer unit 150 extends upwardly from the top of the shoulder housing 124. The brush spacer unit 150 consists of a substantially cylindrical brush spacer base 152, which extends from the top of the shoulder housing 124, and a pair of brush spacer extenders 154, extending from the top of the brush spacer base 152, one on each side of the brush shaft 142. At a distal end, the brush spacer extenders 154 are joined by a brush spacer bridge 156, which passes in front of the brush shaft 142, through a gap in the bristles 144. The brush spacer bridge 156 is faced by a brush spacer pad 158.

Figure 3:
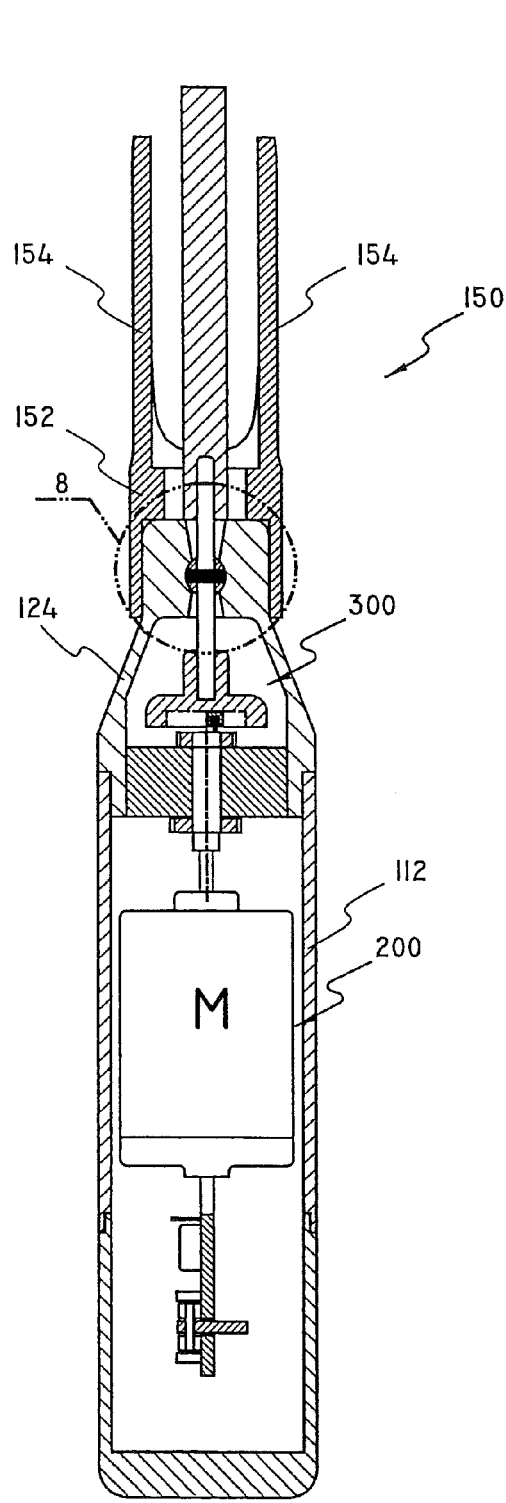
FIG. 3 is a cross sectional view of the toothbrush of the present invention as shown at line 3-3 of FIGS. 1 and 2.
Figure 4:
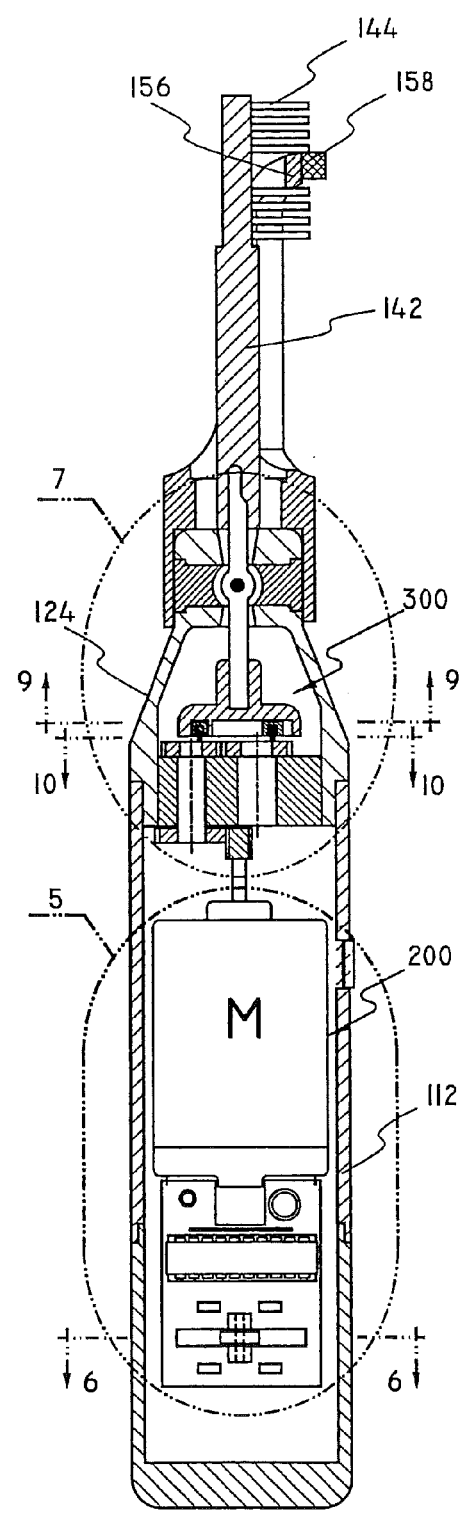
FIG. 4 is a cross sectional view of the toothbrush of the present invention as shown at line 4-4 of FIG. 1.

FIGS. 3 and 4 are front and side cross sectional views, respectively, showing the motor assembly 200 and elliptical drive mechanism 300 as they are mounted within the body housing 112 and shoulder housing 124, the details of which will be discussed herein below.

Figure 5:
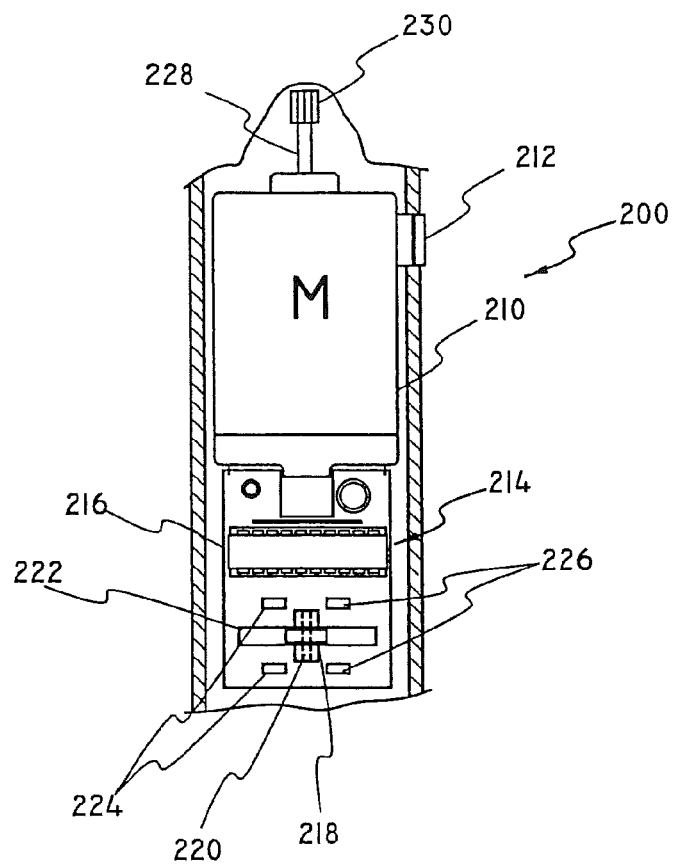
FIG. 5 is a detailed view of the electric motor, electronic control board and direction control mechanism, as isolated at 5 of FIG. 4.
Figure 6:
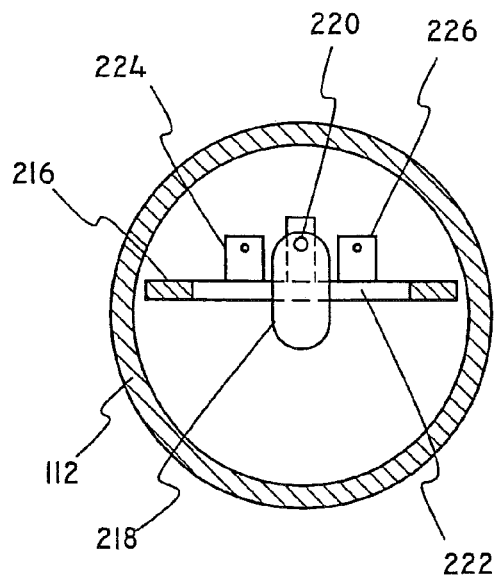
FIG. 6 is a detailed cross sectional view of the electric motor assembly of the toothbrush at line 6-6 of FIG. 4.

Turning now to FIGS. 5 and 6, the motor assembly 200 contains a reversible electric motor 210 which is powered by an electrical energy source (not shown) which could be either an AC power cord attached to a power grid, or a DC battery contained within the body housing 112. In the interest of safety and convenience, a DC battery (not shown) is the preferred power source, whether replaceable or rechargeable. The electric motor 210 is controlled by a three position switch 212 which passes through the wall of the body housing 112. The three positions of the switch 212 consist of "off", and a pair of reversing positions, which are selectively used for brushing the upper or the lower teeth. The electric motor 210 is further controlled by a directional controller 214 which allows the electric motor 210 to automatically reverse its direction of rotation. The directional controller 214 consists of an electronic control board 216 and a pendulum 218 suspended from a pivot point 220 within a slot 222 in the electric control board 216. A pair of infra-red (IR) transceivers 224 and 226 are situated to the right and left, respectively, of the pendulum 218, such that the two elements of each transceiver 224 and 226 are on opposite sides of the slot 222. As the user of the toothbrush 1 changes the angle of the brush in his hand, pendulum 218 swings between the two elements of either transceiver 224 or 226, interrupting the infra-red beam. The interruption of the IR beam causes electronic control board 216 to reverse the direction of rotation of motor drive shaft 228 and drive gear 230, thus reversing the direction of rotation of the brush head 140. After the three position switch 212 is set for either the upper or lower teeth, the directional controller 214 reverses the direction of the electric motor 210 as the angle of the toothbrush 1 changes shifting from the right to left teeth, or front and back of the teeth. It would be evident to one of ordinary skill in the art that a variety of different position sensitive switching mechanisms known in the art, such as, but not limited to, a mercury switch, could be used in lieu of pendulum 218 and IR transceivers 224 and 226, without departing from the spirit of the present invention.

At FIGS. 7, 8, 9 and 10 the elliptical drive mechanism 300, which converts the rotary motion of the motor drive shaft 228 to an elliptical motion of the brush head 140, is illustrated. The elliptical drive mechanism 300 has a body block 310 which engages the interior of the lower end of the shoulder housing 124 such that drive gear 230 at the end of motor drive shaft 228 engages lower gear 312, which is fixedly attached, concentrically, to the lower end of gear shaft 314, which passes upwardly through body block 310. Upper gear 316 is fixedly attached, concentrically, to the upper end of gear shaft 314. A metal pin 318, having a ball head at its upper end, is fixedly attached, eccentrically and normal to the upper surface of upper gear 316. Upper gear 316 engages gear 320, which is rotatably and concentrically attached to a gear shaft 322, fixedly embedded in body block 310. A second metal pin 324, also having a ball head, is fixedly attached, eccentrically and normal to the upper surface of gear 320. The ball head of each of pin 318 and 324 are movably fitted into a cylindrical opening in the bottom of a cube-shaped drive cap 326, 328, respectively.

Figure 7:
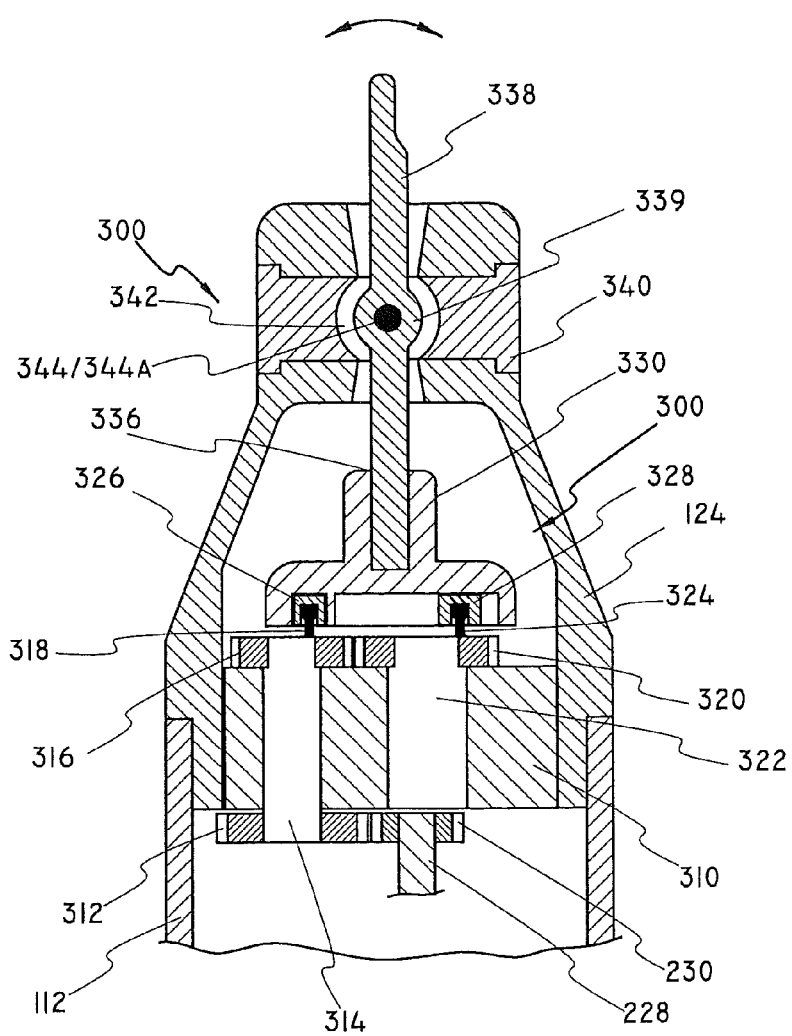
FIG. 7 is a detailed cross sectional view of the joint and elliptical rotation mechanism at line 4-4 of FIG. 1 as isolated at 7 of FIG. 4.
Figure 9:
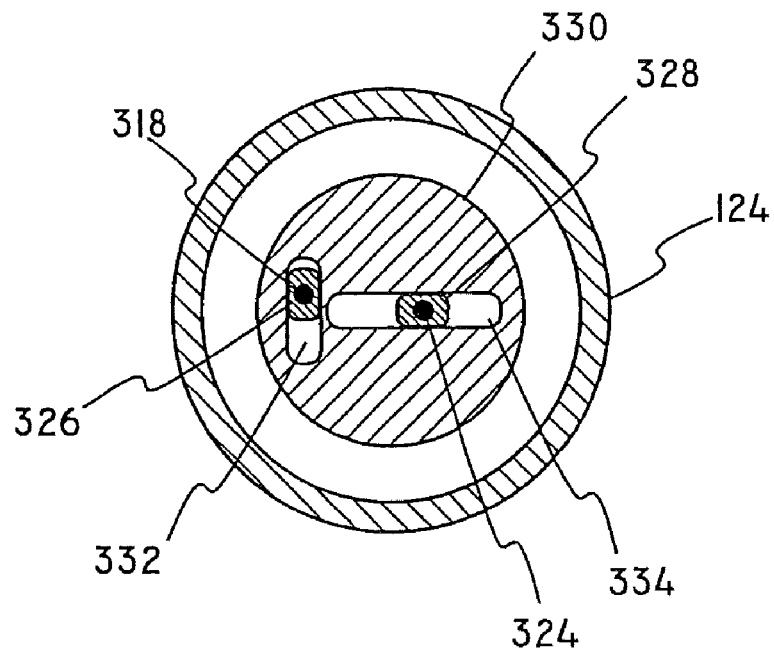
FIG. 9 is a cross sectional view of the elliptical rotation mechanism at line 9-9 of FIG. 4.
Figure 10:
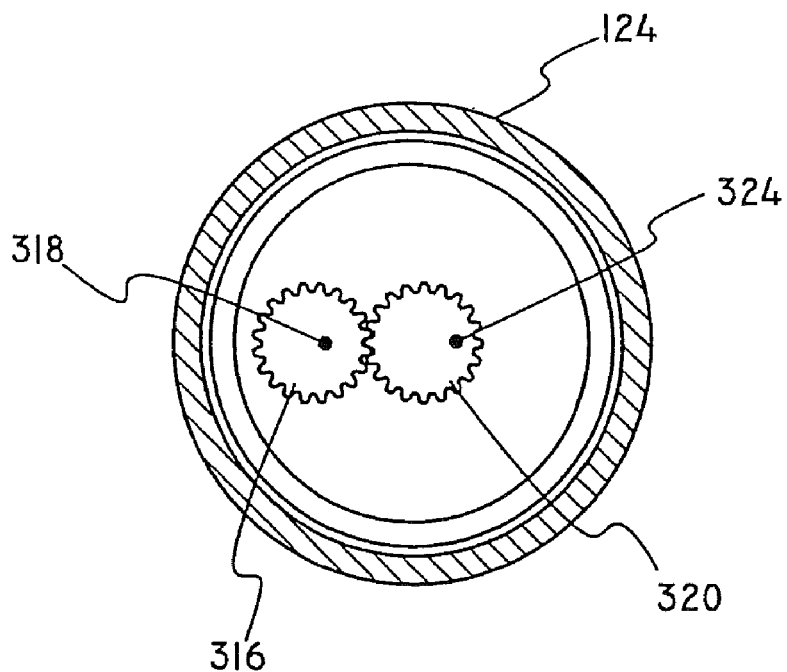
FIG. 10 is a cross sectional view of the elliptical rotation mechanism at line 10-10 of FIG. 4.
Figure 11:
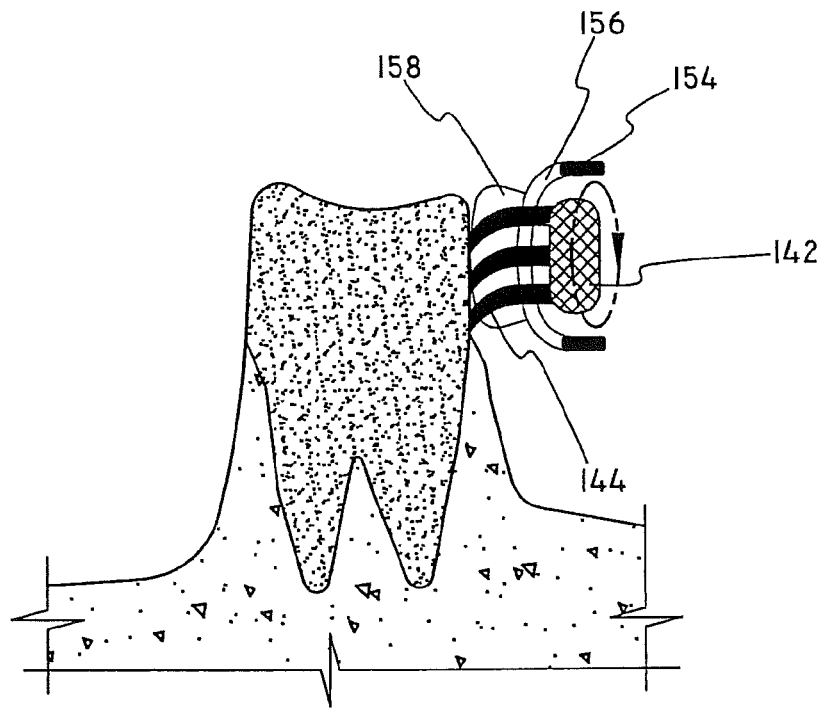
FIG. 11 is a view of the brush head of the tooth brush of the present invention brushing a lower tooth with the bristles at the brushing stroke position of the brush drive shaft's elliptical cycle.
Figure 12:
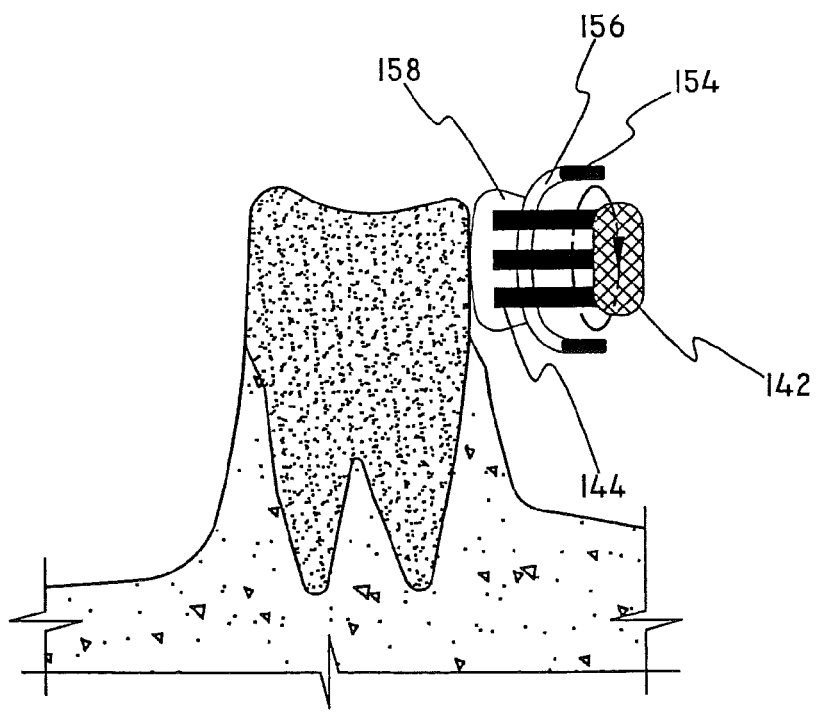
FIG. 12 is a view of the brush head of the tooth brush of the present invention and a lower tooth with the bristles at the recovery portion of the brush drive shaft's elliptical cycle.
Figure 13:
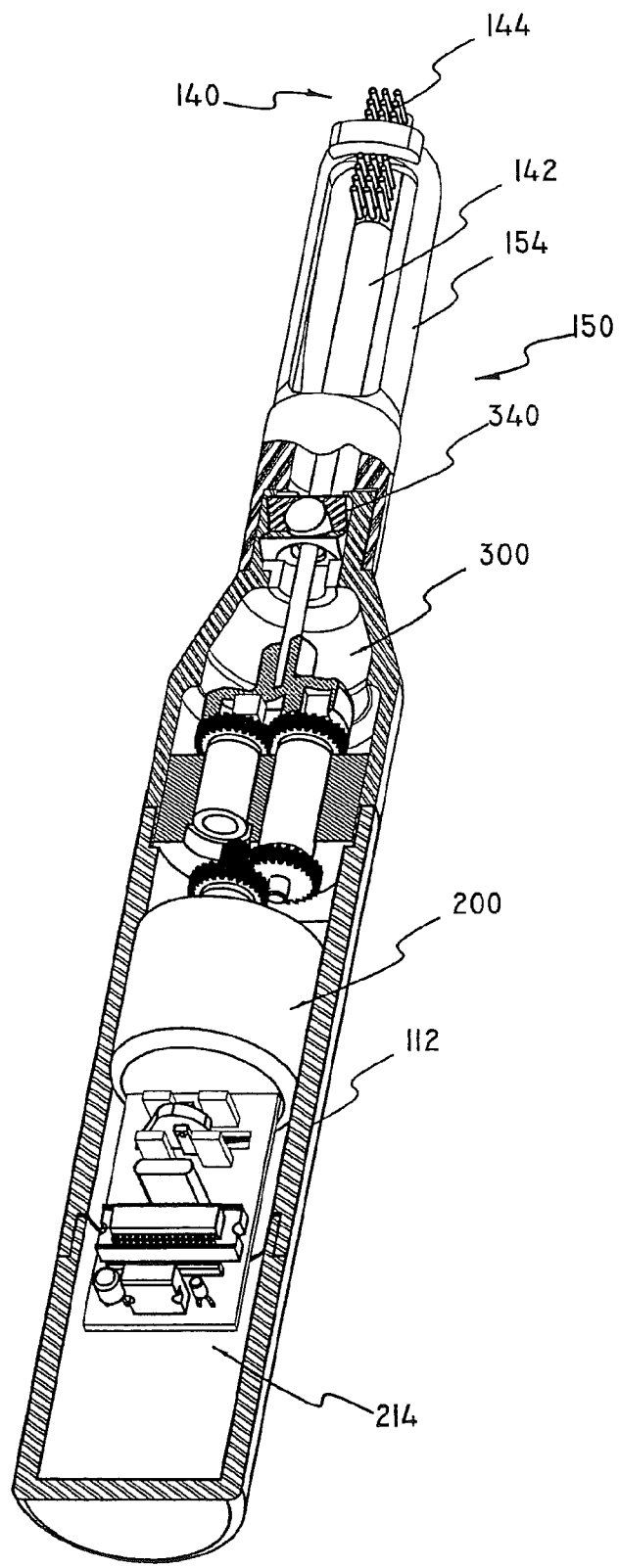
FIG. 13 is a partially cut away perspective view of the toothbrush showing the operating systems with additional detail.
Figure 14:
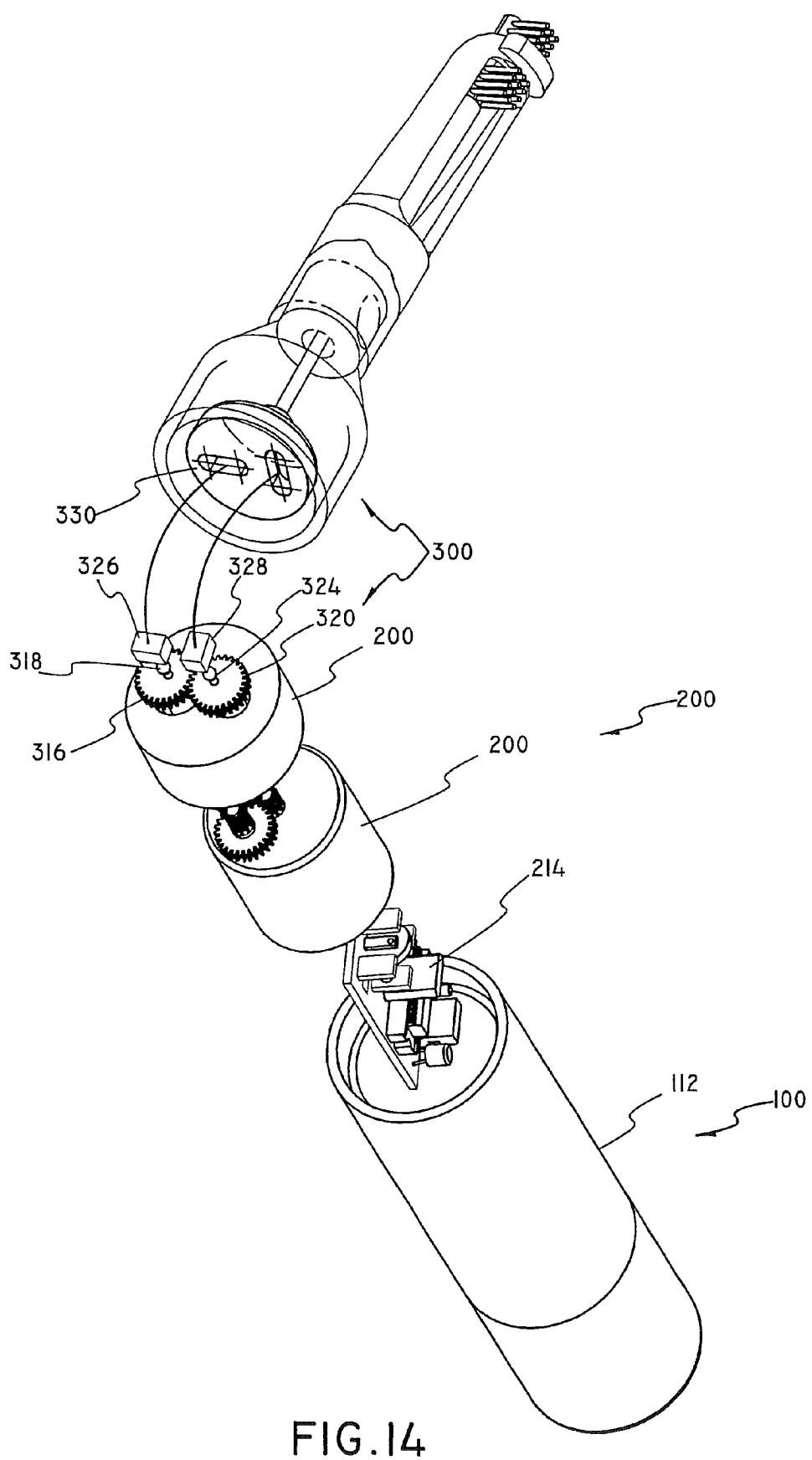
FIG. 14 is an exploded perspective view of the toothbrush showing the interlinking of the operating mechanisms between the various segments of the assembly.

Still referring to FIGS. 7 and 9, an elliptical drive head 330 is of a diameter sufficiently smaller than the interior diameter of shoulder housing 124 (FIG. 2) to allow free movement within shoulder housing 124. Within the lower surface of elliptical drive head 330 are a groove 332 and a groove 334, adapted to movably receive drive caps 326 and 328, respectively.

Groove 332 is located in the lower surface of elliptical drive head 330 near its circumference. It is normal to and centered on a diameter line of elliptical drive head 330. Groove 334, also on the lower surface of elliptical drive head 330, lies along the aforementioned diameter line bisecting, but not joining groove 332 and is disposed such that a first end is proximate groove 332 and a second end is proximate the circumference of elliptical drive head 330. The second end of groove 334 is approximately equidistant from the circumference of elliptical drive head 330 as is the outer edge of groove 332. Within the upper surface of elliptical drive head 330 is a cylindrical drive shaft receptacle 336, adapted to frictionally receive the lower end of brush drive shaft 338.

Drive caps 326, 328 each fit into the grooves 332 and 334, respectively, such that as the gears 316 and 320 turn, thereby moving the drive caps 326, 328 within the grooves 332 and 334, elliptical drive head 330 moves eccentrically within the shoulder housing 124, thereby causing the lower end of the brush drive shaft 338 to move eccentrically. The eccentric motion of the lower end of the brush drive shaft 338 is transferred to the upper end and thus the bristles 144 by the pivot assembly 340, further detailed herein below.

Brush drive shaft 338 is substantially a parallelepiped having a length substantially greater than its substantially square cross section. A rounded protrusion 339 may be located in two of the opposite faces of the length of brush drive shaft 338 proximate its center point provide additional space for a round pivot pin 344 and pivot pin aperture 344A which penetrates brush drive shaft 338 proximate its midpoint, passing between the flat faces of brush drive shaft 338.

Figure 8:
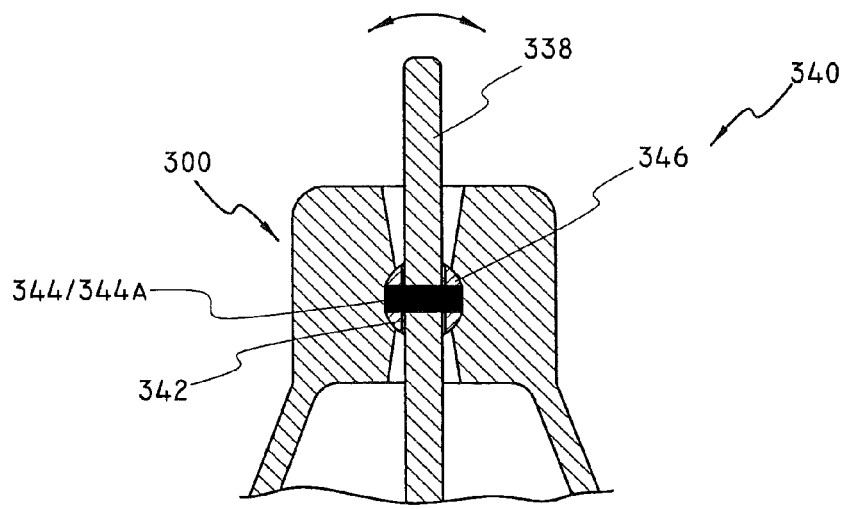
FIG. 8 is a detailed cross sectional view of the joint of the elliptical rotation mechanism at line 3-3 of FIG. 1.

Referring now to FIGS. 7 and 8, there is shown a pivot assembly 340 which occupies a void within shoulder housing 124. The pivot assembly 340 is composed of a substantially solid and rectilinear bar dimensioned so that its ends frictionally engage the interior walls of shoulder housing 124. A pivot aperture 342 within pivot assembly 340 allows brush drive shaft 338 to pass vertically there through. A pivot pin 344 passing through pivot pin aperture 344A of brush drive shaft 338 is anchored at each of its two ends into the interior walls of pivot assembly 340, movably securing brush drive shaft 338 within pivot assembly 340.

Figure 24:
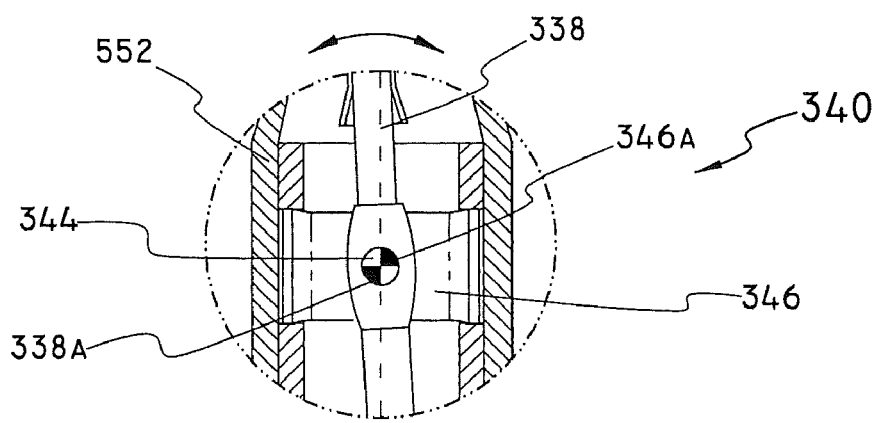
FIG. 24 is a detailed view of the pivot assembly of the toothbrush of the present invention which remains unchanged in the preferred embodiment.
Figure 25:
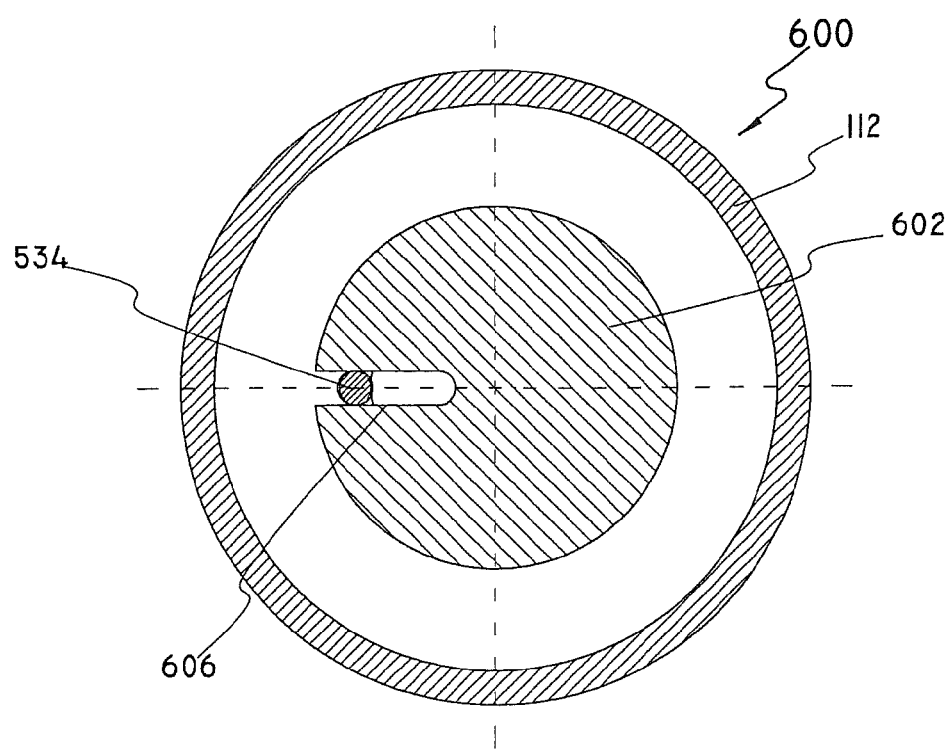
FIG. 25 is a detailed view of the elliptical drive mechanism of the preferred embodiment at line 25-25 of FIG. 20.

Referring now to FIGS. 7, 8 and 24 pivot assembly 340 occupies a void within shoulder housing 124. The pivot assembly 340 consists of a self lubricating cylindrical shape bushing 346 through which the brush drive shaft 338 is passing, entering from center of one side and exiting from the opposite side, perpendicular to the axis of the cylindrical shape bushing 346. The cylindrical shape bushing is rotatably mounted in the pivot assembly 340. Pivot pin 344 is mounted movably inside bushing's apertures 346A on one side and 346B on the opposite side, and passing fixedly through aperture 344A of drive shaft 338. Pivot pin 344 is mounted rotatably perpendicular to the axis of the cylindrical bushing 346 at its middle. Pivot pin 344 is fixedly passing through the brush drive shaft 338. As a result the brush drive shaft 338 has two perpendicular oscillating movements around the longitudinal axis of pivot pin 344 and the longitudinal axis of bushing 346 resulting in an elliptical rotating movement for shaft 338. This creates an elliptical movement for the brush drive shaft and consequently for the brush bristles. Pivot assembly 340 prevents the shaft from rotating around the shaft's axis; consequently, the brush head bristles are always facing the teeth.

It would be evident to one of ordinary skill in the art that various bushings and bearings would be required to facilitate the smooth working of gears and pivot points. These bushing and bearings are well known in the art, therefore they will not be discussed in further detail herein. It would, likewise, be evident to one of ordinary skill in the art that toothbrush 1 could be manufactured of a variety of different materials, but for the sake of economy, various polymerics or plastics would be preferable for housings, shafts and gears, although light metals could also be utilized In operation, switch 212 activates electric motor 210 in one of either a clockwise or counter-clockwise direction, the direction depending on the initial position of pendulum 218. The user, by rotating his wrist, and thereby toothbrush 1, causes pendulum 218 of directional controller 214 to swing in a direction corresponding to the rotation of the wrist. As pendulum 218 breaks the IR beam of either IR transceiver 224 or 226, directional controller 214 is caused to reverse the direction of motor drive shaft 228 of motor 210. Drive gear 230, mounted at the end of motor drive shaft 228, being rotatably engaged with lower gear 312 causes lower gear 312 to drive gear shaft 314, and thus, upper gear 316. Upper gear 316, in turn, drives gear 320, respectively causing elliptical drive head 330 to move elliptically. It will be noted that neither elliptical drive head 330 nor brush drive shaft 338 rotate, but rather, keep a constant orientation in a single direction. Brush drive shaft 338, pivoting about pivot pin 344, transfers the elliptical motion to brush shaft 142 of brush head 140, and thus to the bristles 144 of brush head 140. Again, by twisting the wrist, the user may reverse the direction of elliptical rotation of brush head 140 so that the bristles 114 may travel downwardly for brushing the upper teeth or upwardly for brushing the lower teeth, as is typically recommended by most dental professionals.

Figures 15, 16, 17:
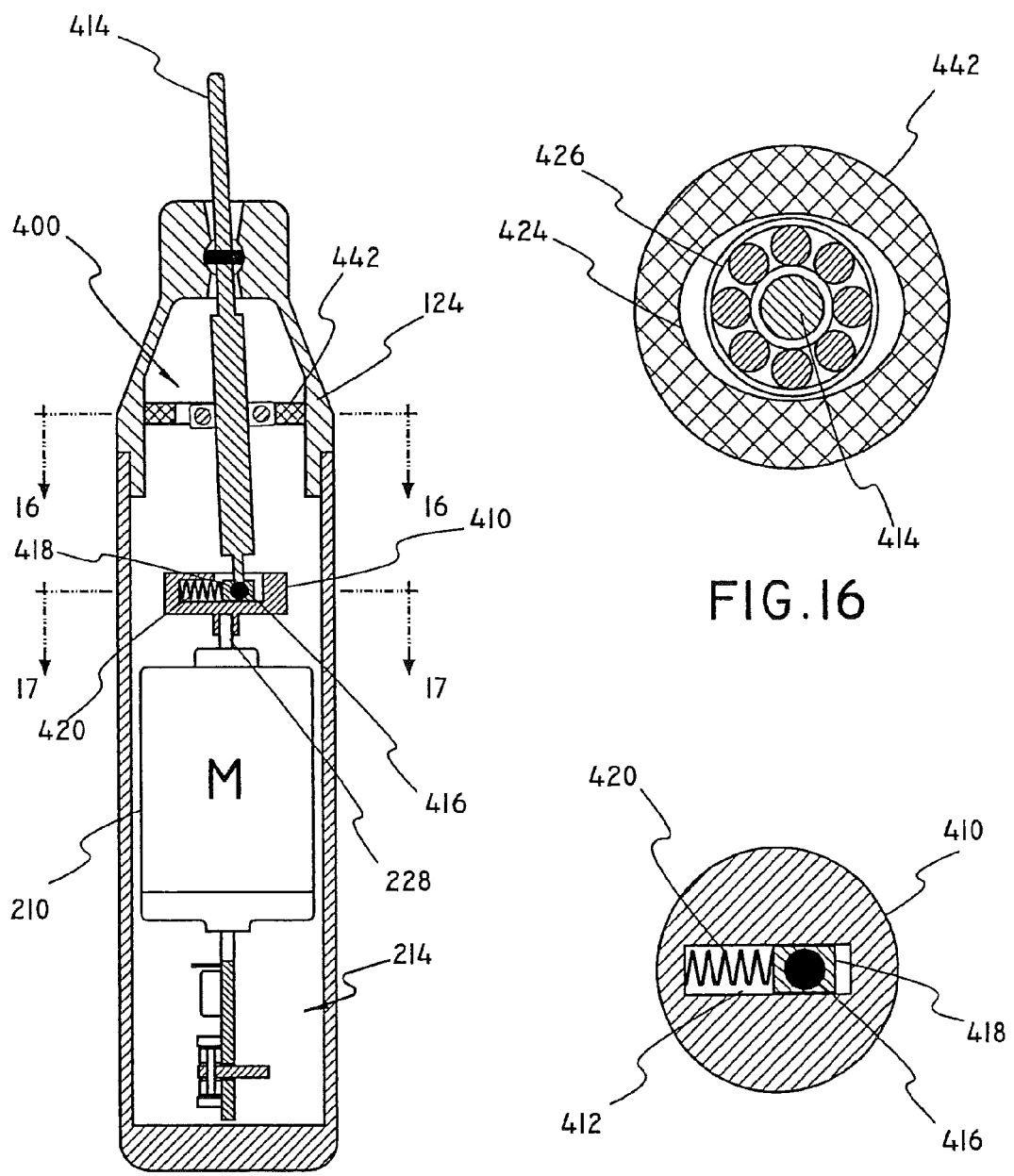
FIG. 15 is a cut away view of an alternative embodiment of the toothbrush having an alternative elliptical rotation mechanism.
FIG. 16 is a cross sectional view of the alternative elliptical rotation mechanism at line 16-16 of FIG. 15.
FIG. 17 is a cross sectional view of the alternative elliptical rotation mechanism at line 17-17 of FIG. 15.

Referring now to FIGS. 15, 16 and 17, an alternate embodiment of an elliptical drive mechanism 400 is presented. Instead of being gear driven, the elliptical drive mechanism of toothbrush 2 is driven directly by electric motor 210. In the alternate embodiment 2, a motor drive shaft 228 terminates in the lower surface of a round drive plate 410, which has a groove 412 disposed in its upper surface. Brush drive shaft 414 has an elongate rectilinear form having a ball capped pin 416 at its lower end, the ball of which is movably secured in a cubic drive cap 418. A spring 420 moveably holds the cubic drive cap 418 eccentrically in position within the groove 412. The rotary motion of motor drive shaft 228 and drive plate 410 is converted to an elliptical motion of brush drive shaft 414 by the movable relationship of pin 416 and drive cap 418, as well as the movable relationship of drive cap 418 within groove 412. A round guide plate 442 is adapted to fit frictionally within the inner walls of shoulder housing 124. Guide plate 442 has an elliptical aperture 424 at its center, which houses a roller bearing assembly 426, which in turn surrounds an end of brush drive shaft 414. Pivot assembly 340 remains unchanged in the alternate embodiment. The combined actions of the eccentricity of the end of brush drive shaft 414 in drive plate 410, the elliptical aperture in guide plate 442 and the fixed pivot point of pivot assembly 340 provide the elliptical motion to brush head 14.

Toothbrush 3, generally presented at FIGS. 18-27 represents the preferred embodiment of the present invention. Toothbrush 3 utilizes an alternative elliptical rotation mechanism, an alternative directional controller and an alternative brushing assembly; pivot assembly 340 remains unchanged in the preferred embodiment.

Figure 18:
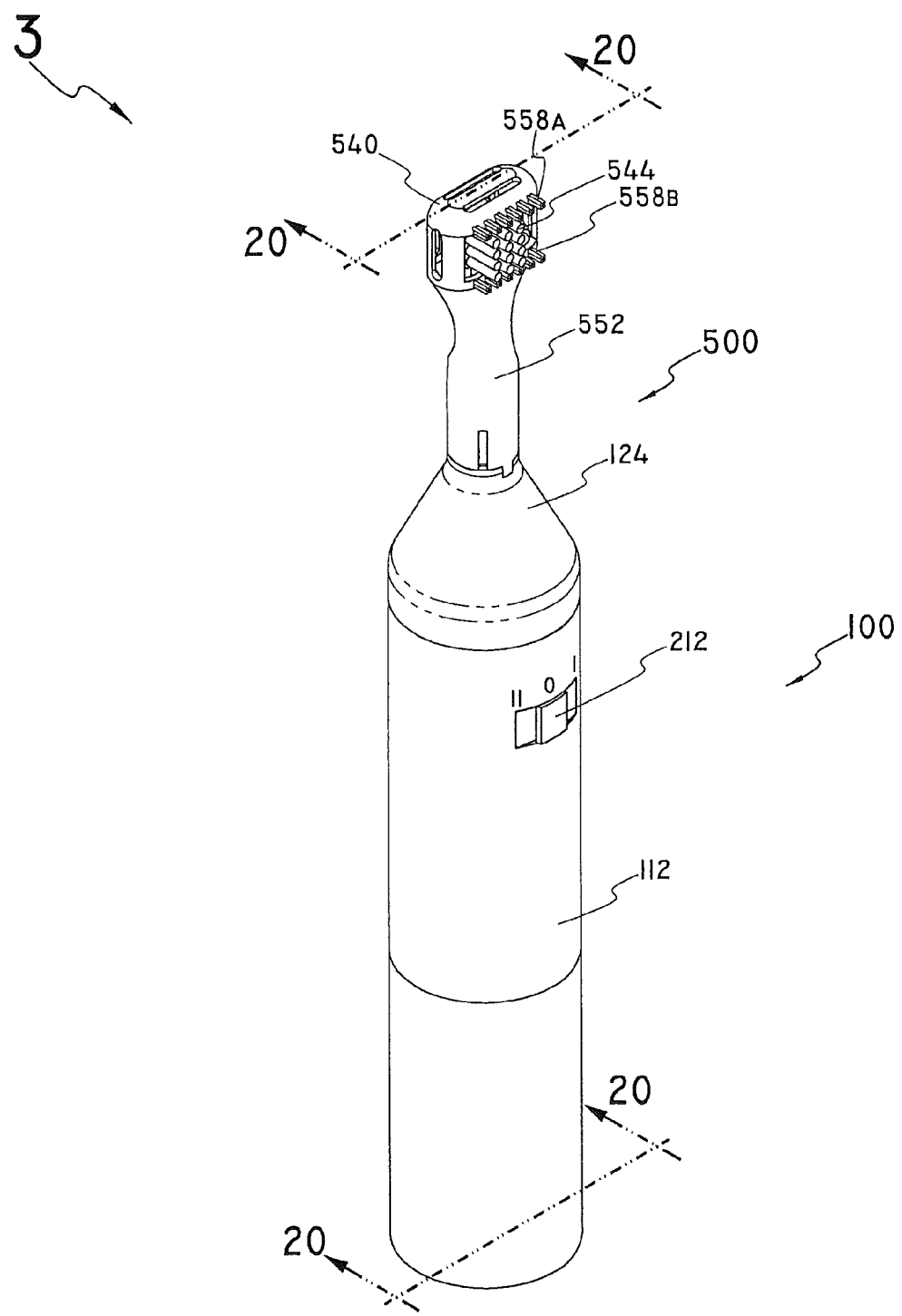
FIG. 18 is a perspective view of the preferred embodiment of the toothbrush having an alternative elliptical rotation mechanism and an alternative directional controller.
Figure 19:
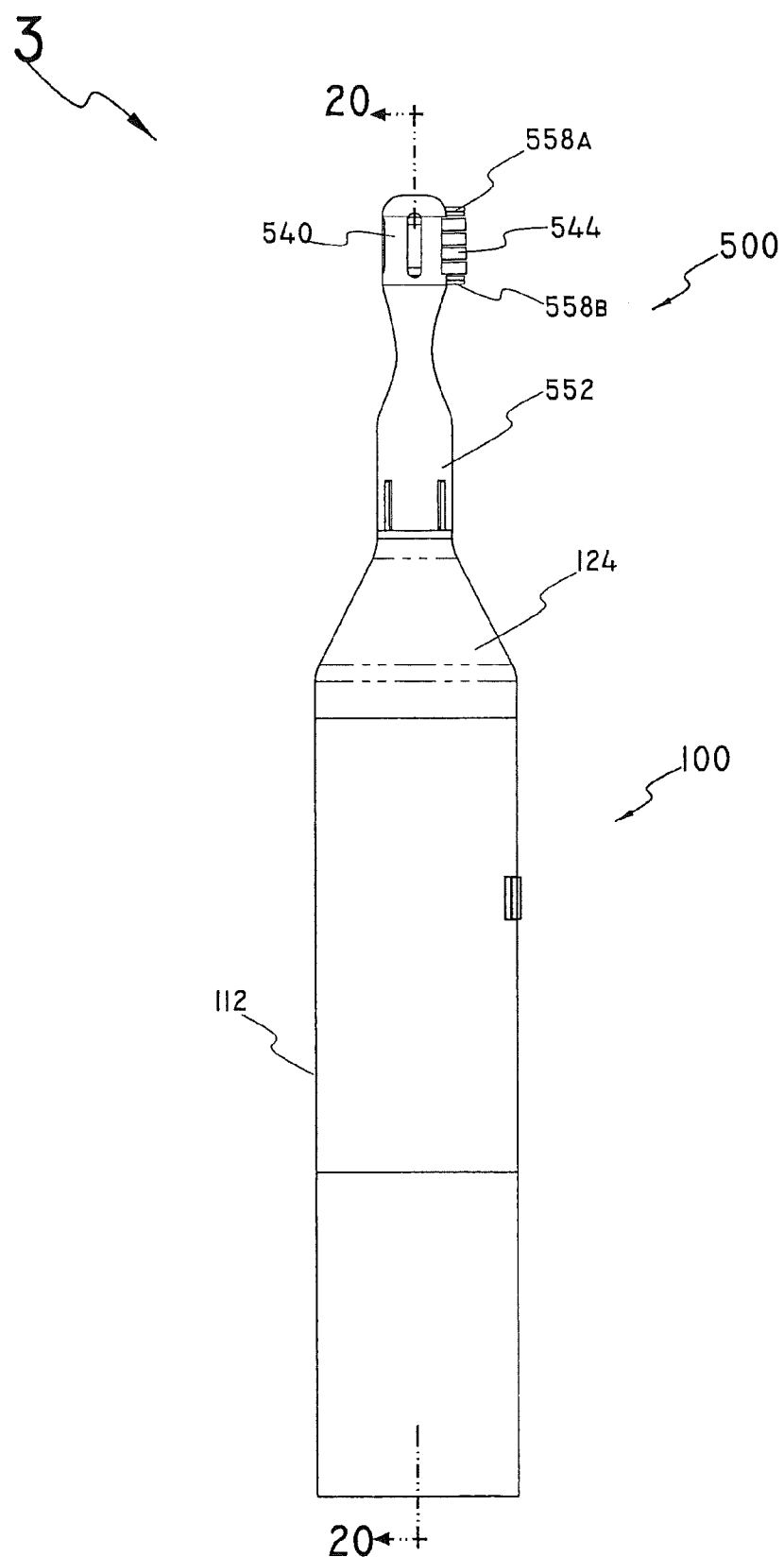
FIG. 19 is a side view of the preferred embodiment of the toothbrush.
Figure 27:
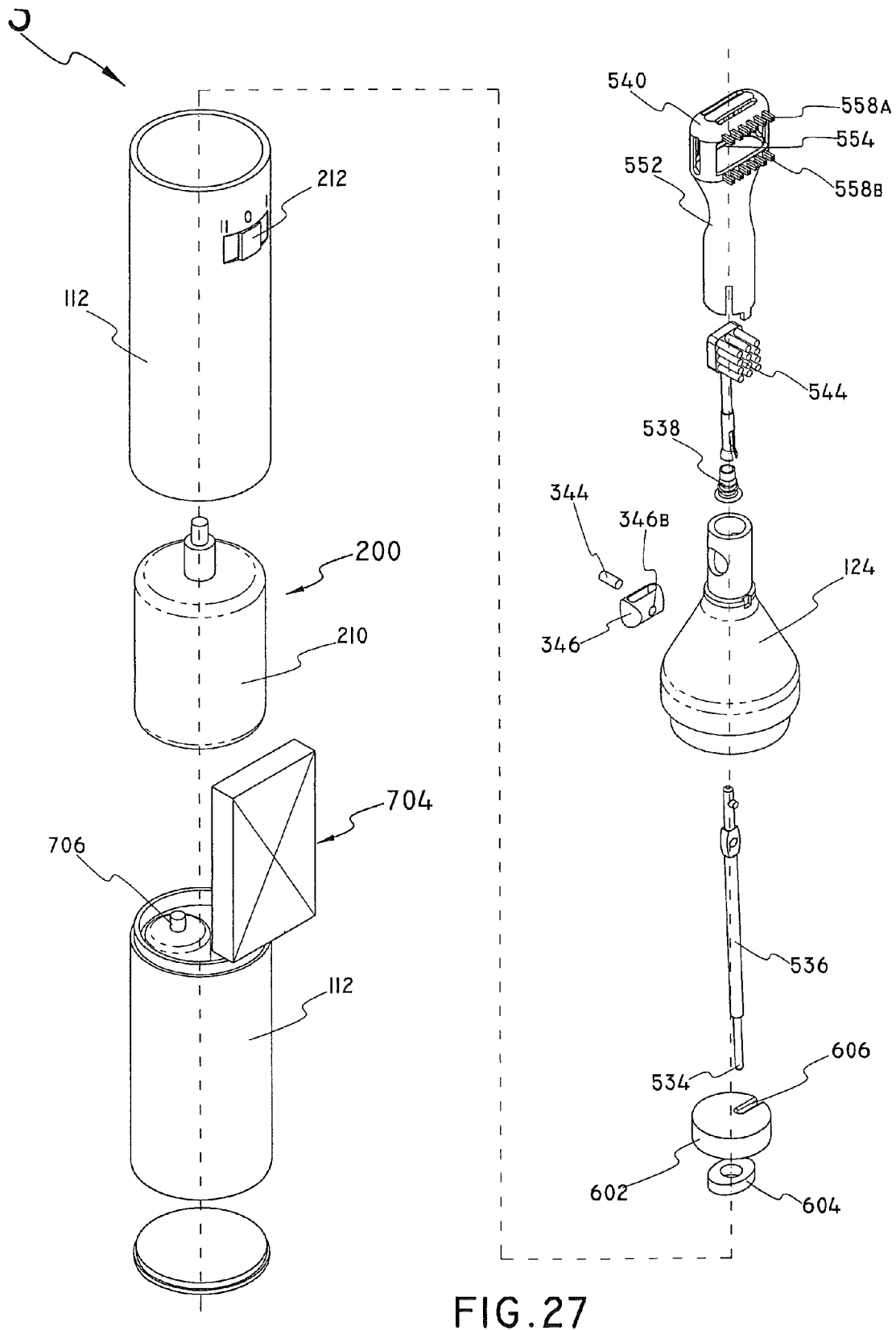
FIG. 27 is an exploded view of the preferred embodiment of the toothbrush.

Referring to FIGS. 18, 19 and 27, an alternative brushing assembly 500 is presented. Brushing assembly 500 is further composed of brush chamber 540 and brush chamber extension 552, brush head 542, bristles 544 and brush head connector 556; while spacing means is composed of upper and lower brush spacers 558A and 558B respectively. It would be evident to one of ordinary skill in the art that brush spacers 558A and 558B may be made of a variety of materials without departing from the spirit of the invention. Brush head 542 and brush chamber 540 are replaceable. Brush chamber extension 552 securely attaches to the top of shoulder housing 124.

Now referring to FIGS. 20, 21, 22, 24 & 25, the alternative elliptical drive mechanism 600 of the preferred embodiment is presented. The oval plate 604 is fixedly attached to the to one end of the motor 210 allowing motor drive shaft 228 rotatably passing through the center of oval plate 604. The motor drive shaft 228 is extended and fixedly attached to the center of rotary plate 602. Brush drive shaft base 534 slidably passes through groove 606 of rotary plate 602; the terminating end of brush drive shaft 534 slidingly rests on the outer edge of oval plate 604. When motor drive shaft 228 begins to rotate around its axis, it forces rotary plate 602 to rotate in the same direction. The terminating end of drive shaft base 534 begins to slide around the outer edge of oval plate 604. As the terminating end of brush drive shaft base 534 moves on the outer edge of oval plate 604, drive shaft base 534 slides inside groove 606 of rotary plate 602 along the longitudinal axis of groove 606 accordingly.

Still referring to FIGS. 20, 21, 22, 24 & 25, brush drive shaft 536 is connected to brush head connector 556 which passes through oval-shaped brush chamber aperture 554. Brush head connector 556 touches the inner wall of aperture 554, and when the drive shaft base 534 begins its elliptical movement, brush head connector 556 begins to slide against the inner wall of aperture 554. Therefore, the movement of brush head connector 556 inside oval aperture 554 is limited to the circumference of aperture 554. This prevents brush connector 556 from rotating beyond the inner wall of the aperture 554. On the other hand the movement of brush drive shaft base 534 is limited to the circumference of oval plate 604. Brush drive shaft base is constantly touching the outer edge of oval plate 604, and brush head connector 556 is constantly touching the inner wall of brush chamber aperture 554. The diameters of oval plate 604 and aperture 554 are configured so that at any given time, the position of brush shaft base 534 on oval plate 604 corresponds to the exact opposite position of brush head connector 556 inside aperture 554 and vice versa. The combination of the movements of brush drive shaft 536, the movement of brush head connector 556 inside aperture 554, drive shaft base 534 around oval plate 604, and pivot assembly 340 create an elliptical movement for brush head 542 and consequently for bristles 544.

Figure 20:
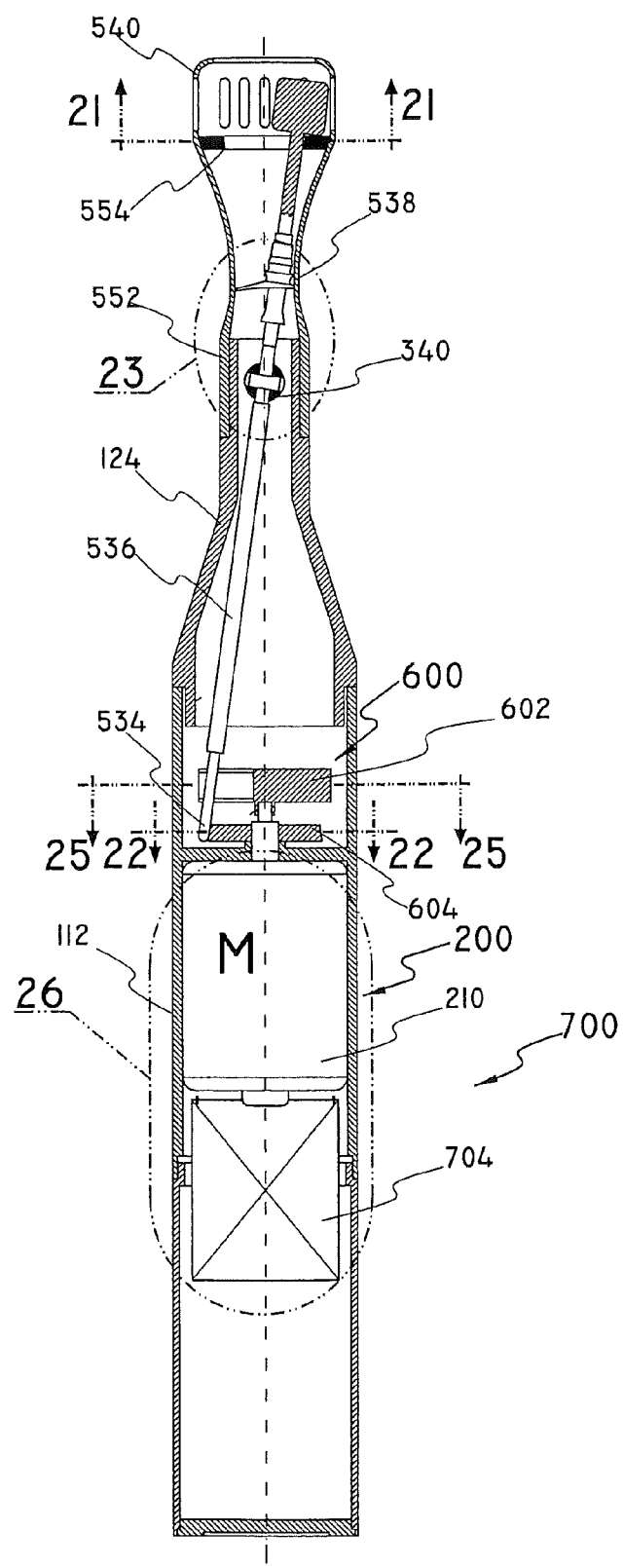
FIG. 20 is a cross sectional view of the preferred embodiment at line 20-20 of FIG. 18.
Figure 21:
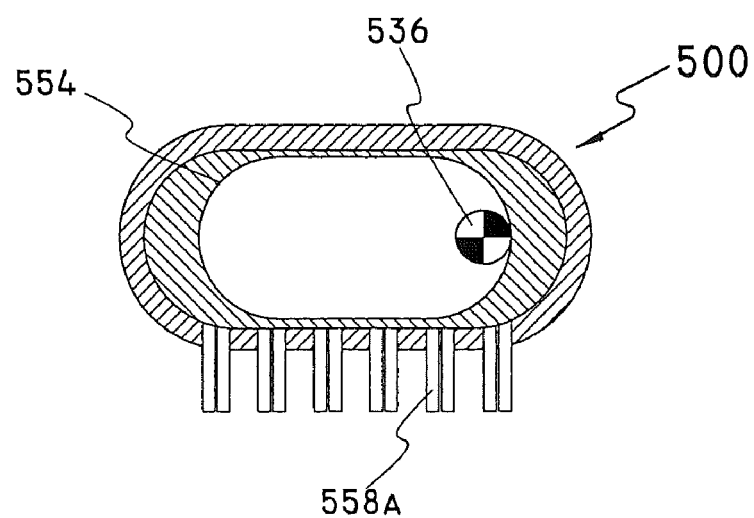
FIG. 21 is a cross sectional view of the brush head of the preferred embodiment at line 21-21 of FIG. 20.
Figure 22:
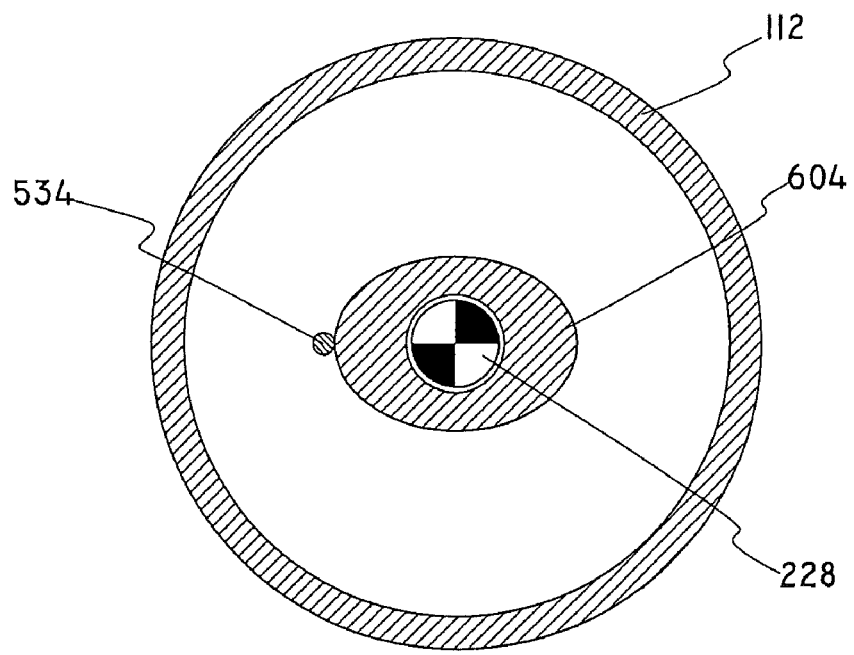
FIG. 22 is a cross sectional view of the preferred embodiment at line 22-22 of FIG. 20.
Figure 23:
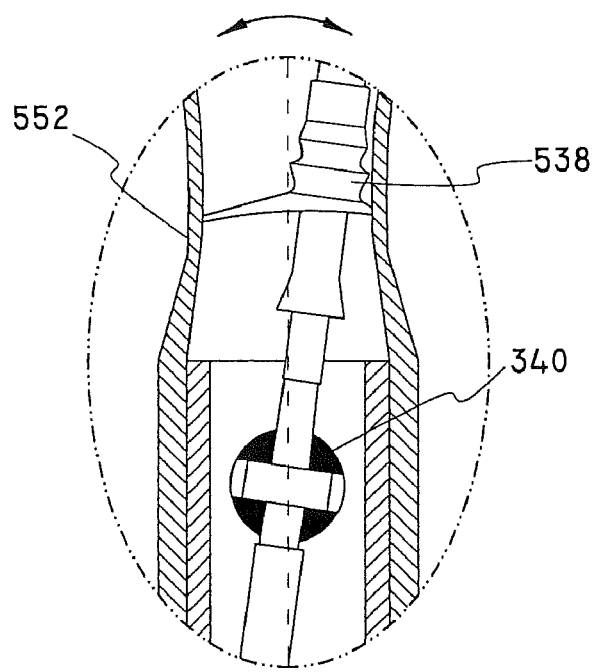
FIG. 23 is a detailed view of the sealing boot of the preferred embodiment of the invention as isolated at 23 of FIG. 20.

Now referring to FIGS. 20 and 23, flexible sealing boot 538, which is similar to a gear boot in an automobile, prevents liquid from penetrating inside the toothbrush; flexible sealing boot 538 does not limit the movement of brush head connector 556 and brush drive shaft 536.

Referring to FIG. 27, groove 560 is located on brush head connector 556. When connecting brush head connector 556 to brush drive shaft 536, button 562 slides inside groove 560 and secures brush head connector 556 into place; this prevents brush head connector 556 from rotating around its own axis, and therefore ensures that brush head 542 and bristles 544 always face the user's teeth.

Figure 26:
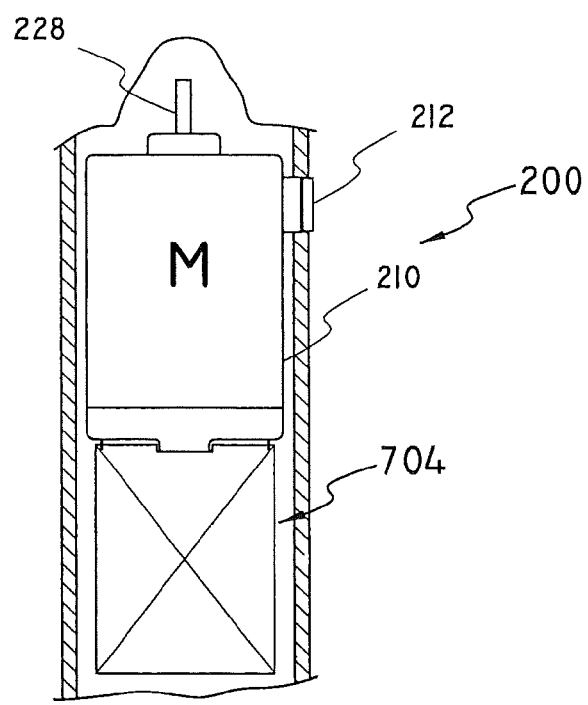
FIG. 26 is a detailed view of the motor assembly of the toothbrush showing the alternative direction controller as isolated at 26 of FIG. 20.

Referring to FIGS. 20, 26 and 27, the alternate directional controller 700 includes accelerometer 704. When the user rotates his/her wrist and thereby toothbrush 3, the change of orientation is sensed by accelerometer 704 which causes motor drive shaft 228 to reverse direction accordingly. As a result, the brushing direction can be accordingly changed when brushing upper or lower teeth. Battery 706 can be either a rechargeable or a disposable battery.

It is to be understood that the present invention is not limited to the embodiments described above, but encompasses any and all embodiments within the scope of the following claims.

What is claimed is:

1. An electric toothbrush comprising:

housing means for giving said toothbrush form, said housing means comprising an elongate, substantially hollow handle portion and having at an upper end thereof a substantially hollow shoulder portion, said housing means supporting the following working elements of said toothbrush:

brushing means for brushing a user's teeth said brushing means comprising:
  a brush drive shaft,
  a brush head,
  a brush head connector having two ends, said brush head connector being securely attached to said brush head at one end and to said brush drive shaft at the other end, in such way preventing said brush drive shaft and said brush head from rotating around their own axes, and
  a brush chamber having an oval aperture with inner walls, said brush head connector passing therethrough and said brush head connector being capable of sliding against the inner walls of said aperture, spacing means for spacing said brushing means away from the surface of a user's teeth, sealing means for preventing liquid from entering inside said toothbrush, power means for providing power to said toothbrush, motor means for converting said power into rotary motion of a drive shaft of said motor means, switch means for turning said motor means on and off and controlling the direction of rotation of the drive shaft of said motor means as determined by the teeth to be brushed, from among the group consisting of the upper teeth and the lower teeth, and conversion means for converting the rotary motion of said motor means drive shaft to an elliptical motion of said brushing means, wherein said conversion means comprises an elliptical drive mechanism, said elliptical drive mechanism comprising:
  said oval aperture on said brush chamber,
  a pivot assembly,
  a rotary plate receiving an end of said motor drive shaft, such that rotary motion of said motor drive shaft results in rotary motion of said rotary plate, said rotary plate having a groove through which an end of said brush drive shaft passes, said end of said brush drive shaft being able to slide inside said groove along a longitudinal axis of said groove and an oval plate having an outer edge and a center, a base of said motor drive shaft passing through said center of said oval plate, wherein an end of said brush drive shaft slides against said outer edge of said oval plate during said elliptical motion of said brushing means.

2. An electric toothbrush, as defined in claim 1, wherein the diameters of said oval aperture on said brush chamber and the diameters of said oval plate are configured in such a way that the position of one end of said brush shaft on said outer edge of said oval plate corresponds to the exact diametrically opposite position of said brush head connector on said inner wall of said brush chamber oval aperture, and the combination of movement of one end of said brush shaft on said outer edge of said oval plate, movement of said brush shaft in said pivot assembly, and movement of said brush head extension on said inner wall of said brush chamber oval aperture cause an elliptical movement of said brush head, resulting, when in use, in said bristles brushing teeth in one direction, always starting from gum lines and ending at biting edge of said teeth and completely detaching from said teeth before moving through a recovering reverse motion.

3. An electric toothbrush, as defined in claim 1, wherein said pivot assembly comprises:

a cylindrically shaped bushing rotatably attached about its longitudinal axis within said pivot assembly, said bushing allowing said brush drive shaft to pass therethrough with said brush drive shaft being perpendicular to said longitudinal axis of said bushing, said bushing having two apertures, and a pivot pin passing through and being fixedly secured to said brush drive shaft and being perpendicular to the longitudinal axis of said brush drive shaft, said pivot pin further passing through said two apertures of said bushing and being movable relative thereto.

4. An electric toothbrush, as defined in claim 1, wherein said switch further comprises a position sensitive switch which automatically reverses said direction of rotation of said drive shaft based on the angle at which said toothbrush is held in a user's hand after said initial direction of rotation has been established, for said upper and/or lower teeth and wherein said position sensitive switch further comprises an accelerometer sensing the angle at which said toothbrush is being held, the direction of rotation of said motor drive shaft being reversible depending on the angle sensed by said accelerometer.

* * * * *